United States Patent
Fontana et al.

(10) Patent No.: US 8,076,351 B2
(45) Date of Patent: Dec. 13, 2011

(54) CAMPTOTHECIN DERIVATIVES WITH ANTITUMOR ACTIVITY

(75) Inventors: Gabriele Fontana, Milan (IT); Ezio Bombardelli, Groppello Cairoli (IT); Carla Manzotti, Milan (IT); Arturo Battaglia, Bologna (IT); Maria Grazia Allegri, legal representative, Imola (IT); Cristian Samori, Forli (IT)

(73) Assignee: Indena S.p.A., Milan (IT)

( * ) Notice: Subject to any disclaimer, the term of this patent is extended or adjusted under 35 U.S.C. 154(b) by 254 days.

(21) Appl. No.: 12/374,799

(22) PCT Filed: Jul. 12, 2007

(86) PCT No.: PCT/EP2007/006218
§ 371 (c)(1),
(2), (4) Date: Jun. 8, 2009

(87) PCT Pub. No.: WO2008/011992
PCT Pub. Date: Jan. 31, 2008

(65) Prior Publication Data
US 2010/0063082 A1    Mar. 11, 2010

(30) Foreign Application Priority Data
Jul. 26, 2006 (IT) .................. MI06A1475

(51) Int. Cl.
*A61K 31/4745* (2006.01)
*C07D 491/22* (2006.01)
(52) U.S. Cl. .......................... 514/279; 546/41
(58) Field of Classification Search .................. 514/279; 546/41
See application file for complete search history.

(56) References Cited

U.S. PATENT DOCUMENTS

| | | | |
|---|---|---|---|
| 5,834,479 | A | 11/1998 | Terasawa et al. |
| 5,972,955 | A | 10/1999 | Duvvuri et al. |
| 6,177,439 | B1 | 1/2001 | Duvvuri et al. |
| 6,214,836 | B1 | 4/2001 | Duvvuri et al. |
| 6,265,413 | B1 | 7/2001 | Jew et al. |

FOREIGN PATENT DOCUMENTS

WO    0066127 A1    11/2000

OTHER PUBLICATIONS

Sugimori et al., "Antitumor Agents VI Synthesis and Antitumor Activity of Ring A-, Ring B-, and Ring C-Modified Derivatives of Camptothecin", Heterocycles 38(1):81-94 (1994).

*Primary Examiner* — Charanjit Aulakh
(74) *Attorney, Agent, or Firm* — Porzio, Bromberg & Newman, P.C.

(57) ABSTRACT

Novel camptothecin derivatives having antitumor activity, the processes for the preparation thereof, the use thereof as antitumor drugs and pharmaceutical compositions containing them.

12 Claims, No Drawings

CAMPTOTHECIN DERIVATIVES WITH ANTITUMOR ACTIVITY

CROSS REFERENCE TO RELATED APPLICATION

This is a National Stage of International Application PCT/EP2007/006218, filed 12 Jul. 2007, which claims the benefit of Application No. M12006A001475, filed in Italy on 26 Jul. 2006, the disclosures of which Applications are incorporated by reference herein.

The present invention relates to novel camptothecin derivatives having antitumor activity, the processes for the preparation thereof, the use thereof as antitumor drugs and pharmaceutical compositions containing them.

BACKGROUND OF THE INVENTION

Camptothecin is an alkaloid extracted from *Camptotheca acuminata* (Nyssaceae), first described by Wall and Wani in 1966 (J. Am. Chem. Soc. 1966, 88, 3888-3890). Camptothecin, albeit endowed with wide spectrum antitumor activity, especially against colon tumor and other solid tumors and leukemias, is not used in therapy due to its high toxicity, which is particularly manifested in the form of hemorrhagic cystitis, gastrointestinal toxicity and myelosuppression.

A number of camptothecin analogues have been synthesized in order to obtain compounds having low toxicity and high solubility. At present, two drugs are used in clinical practice, namely CPT-11 and topotecan. Other derivatives, such as belotecan, rubitecan, exatecan, gimatecan, pegamotecan, lurtotecan, karenitecin, afeletecan, homocamptothecin, diflomotecan, and many others, are undergoing clinical experimentation. Compound CPT-11 is a highly soluble prodrug for 10-hydroxy-7-ethylcamptothecin (commonly known as SN-38), approved for the treatment of many solid tumors and ascites (colorectal, skin, stomach, lung, cervice, ovary, non-Hodgkin lymphoma).

Topotecan is a compound soluble in physiological solution, active against the tumors of the lung, stomach, liver, ovary, breast, prostate, esophagus, rectum, soft tissues sarcomas, head and neck, glioblastoma, chronic and acute myelocytic leukemias. Topotecan shows, however, important side effects such as neutropenia and thrombocytopenia.

Lurtotecan is a more soluble derivative, having activity in tumors of the neck, ovary, breast, colo-rectal, and pulmonary microcytoma. However, Lurtotecan also has hematic toxicity.

Rubitecan is a prodrug for the oral use effective against tumors of the pancreas, ovary and breast.

Camptothecin and its analogues, as is the case with all topoisomerase I inhibitors, are effective against tumors resistant to conventional drugs, including topoisomerase II inhibitors; maintain high topoisomerase levels during the whole cell cycle; do not induce multi-drug resistance (Pgo or MRP) or detoxifying metabolism mediated by the enzyme.

Research is now focused on novel inhibitors of the topoisomerase I having lower toxicity than the presently used drugs.

Open-ring camptothecin derivatives show high protein binding (in particular with albumin) and low distribution in the tumor tissues. As a consequence, the product accumulates in the body and tumors are poorly affected.

Conversely, the high lipophilicity of the lactone form promotes the adhesion of camptothecin derivatives to cell membranes, particularly erythrocytes, affecting the tissue/plasma distribution ratio. For this reason, research is being focused towards two alternative approaches: a) design of low protein binding products still having good solubility; b) design of highly potent products having therapeutical effect even at extremely low doses.

Modifications at the 7-, 9-, 10- and 11-positions usually proved well tolerated while not affecting the stability of the DNA-Topoisomerase I-camptothecin ternary complex, the formation of which is responsible for the antitumor activity of the compounds.

Products with 20R configuration proved either inactive or very less active than the products with 20S configuration—which coincides with the natural configuration.

As a rule, modifications at the 5-position are considered unfavourable to the formation of the ternary complex, whereas modifications at the pyridone rings D and E have bee reported to be deleterious to the activity of the product.

DISCLOSURE OF THE INVENTION

In a first aspect, the invention relates to camptothecin derivatives of general formula I:

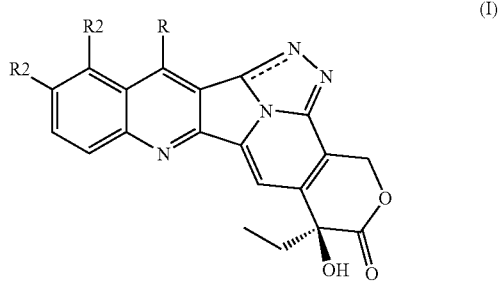

(I)

wherein:
R is alkyl, aminoalkyl, hydroxyalkyl, nitrile, alkoxymino, aryloxymino, silylalkyl;
R1 is hydrogen, hydroxy, alkoxy, aminoalkyl;
R2 is hydrogen, hydroxy, alkoxy, aminoalkyl, optionally protected hydroxyl;
wherein the alkyl, alkoxy, aminoalkyl or alkoxymino groups can contain 1 to 8, preferably 1 to 4 carbon atoms, in a straight or branched chain, whereas the aryloxymino group can contain 5 to 10 carbon atoms;
the pharmaceutically acceptable salts, isomers, enantiomers, diastereomers thereof and corresponding mixtures.

The compounds of the invention show low protein binding and have good solubility and high potency even at very low doses.

The preferred synthetic route for the preparation of the compounds of the invention is illustrated in the following scheme and substantially involves the following steps:
 a) protection of the precursor hydroxy groups;
 b) derivatization at 5- with N,N-diprotected hydrazine;
 c) optional conversion of the pyridone ring to thiopyridone ring;
 d) removal of the protective groups with concomitant cyclization;
 e) optional aromatization of the pyrazole ring;

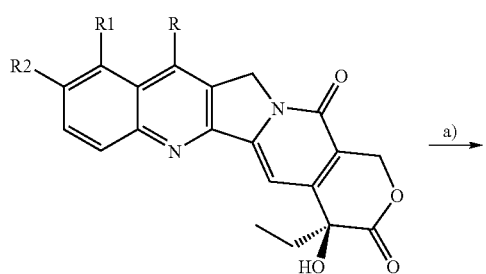

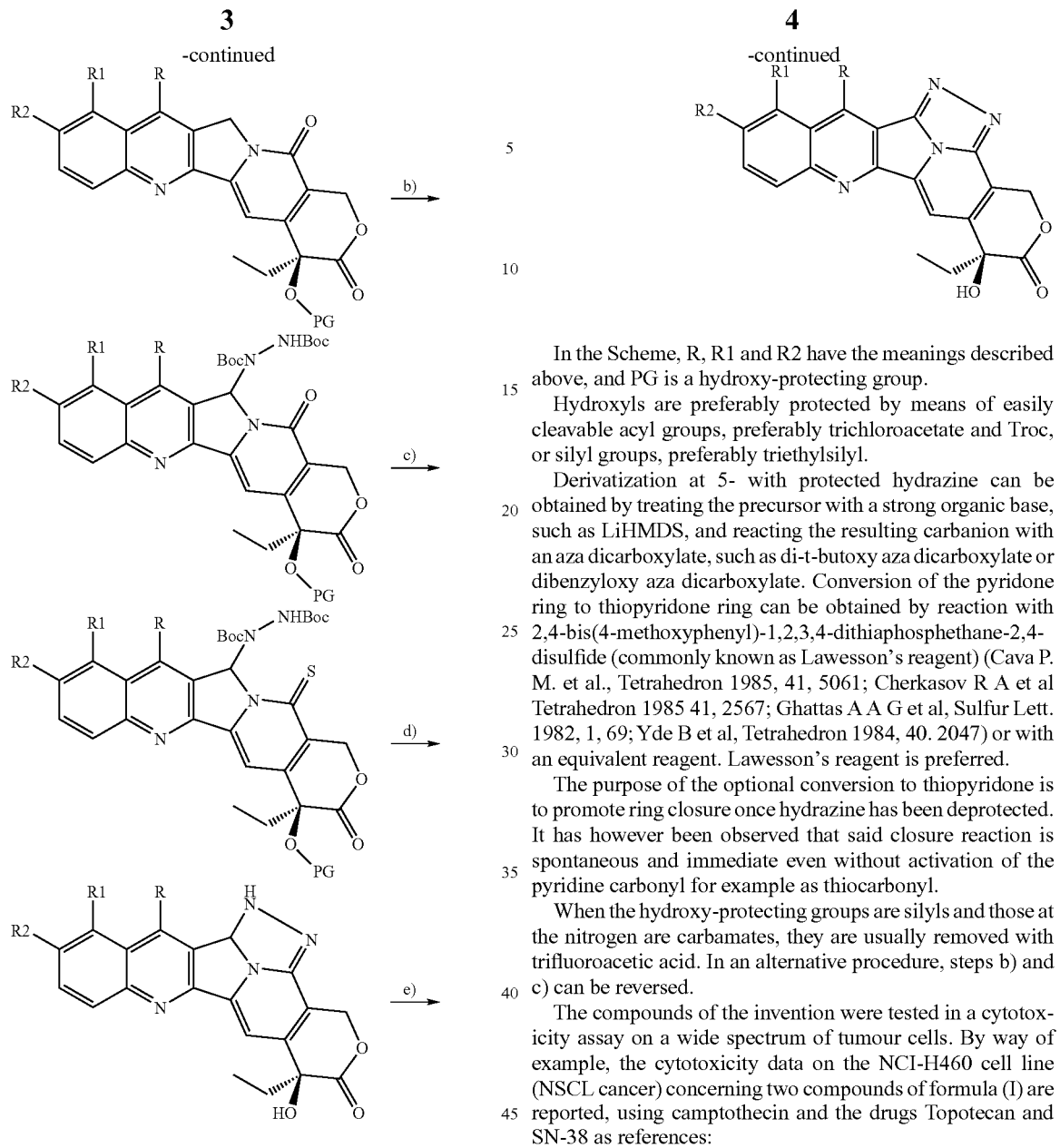

In the Scheme, R, R1 and R2 have the meanings described above, and PG is a hydroxy-protecting group.

Hydroxyls are preferably protected by means of easily cleavable acyl groups, preferably trichloroacetate and Troc, or silyl groups, preferably triethylsilyl.

Derivatization at 5- with protected hydrazine can be obtained by treating the precursor with a strong organic base, such as LiHMDS, and reacting the resulting carbanion with an aza dicarboxylate, such as di-t-butoxy aza dicarboxylate or dibenzyloxy aza dicarboxylate. Conversion of the pyridone ring to thiopyridone ring can be obtained by reaction with 2,4-bis(4-methoxyphenyl)-1,2,3,4-dithiaphosphethane-2,4-disulfide (commonly known as Lawesson's reagent) (Cava P. M. et al., Tetrahedron 1985, 41, 5061; Cherkasov R A et al Tetrahedron 1985 41, 2567; Ghattas A A G et al, Sulfur Lett. 1982, 1, 69; Yde B et al, Tetrahedron 1984, 40. 2047) or with an equivalent reagent. Lawesson's reagent is preferred.

The purpose of the optional conversion to thiopyridone is to promote ring closure once hydrazine has been deprotected. It has however been observed that said closure reaction is spontaneous and immediate even without activation of the pyridine carbonyl for example as thiocarbonyl.

When the hydroxy-protecting groups are silyls and those at the nitrogen are carbamates, they are usually removed with trifluoroacetic acid. In an alternative procedure, steps b) and c) can be reversed.

The compounds of the invention were tested in a cytotoxicity assay on a wide spectrum of tumour cells. By way of example, the cytotoxicity data on the NCI-H460 cell line (NSCL cancer) concerning two compounds of formula (I) are reported, using camptothecin and the drugs Topotecan and SN-38 as references:

| Name | Formula | NCI-H460 IC50 (μg/mL) Cell count |
|---|---|---|
| Topotecan | 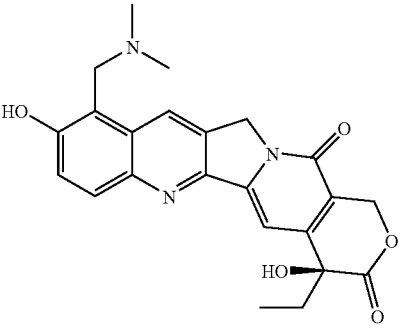<br>FW = 421<br>C23H23N3O5 | 0.63 ± 0.44 |
| SN38 | 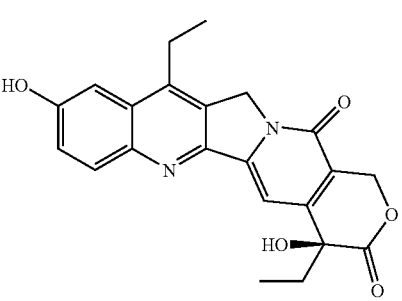<br>FW = 392.42<br>C22H20N2O5 | 0.0865 ± 0.0049 |
| IDN 6132 | 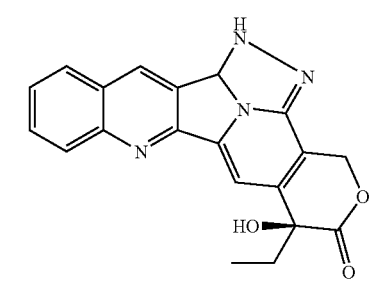<br>FW = 363.38<br>C20H17N3O4 | 17 ± 4.25 |
| IDN 6137 | 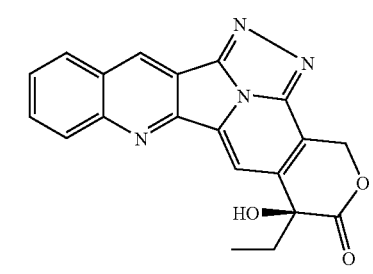<br>FW = 358.36<br>C20H14N4O3 | 3.8 ± 1.08 |

The most active compounds were evaluated in a DNA cleavage assay measuring the active concentration and damage persistence (see the section 'Examples'). The derivatives of formula (I) surprisingly show higher persistence in blocking DNA replication than the reference standards (particularly topotecan and camptothecin), while maintaining an effective cytotoxic activity.

In a further aspect, the invention relates to pharmaceutical compositions containing a compound of formula (I) together with pharmaceutically acceptable carriers and excipients. The pharmaceutical forms suitable to the oral or parenteral administration of the compounds (I) can be solid, preferably capsules, tablets and granules, or liquid, preferably injectable or infusion solutions.

The suitably formulated compounds of the invention can be used for the treatment of solid tumors and leukemias, in particular tumors of the lung, ovary, breast, stomach, liver, prostate, soft tissue sarcomas, head and neck, esophagus, pancreas, colon, rectum, glioblastoma, chronic and acute myelocytic leukemias.

EXAMPLES

Example I

20-OTES-camptothecin

Camptothecin (0.100 g, 0.287 mmol), is suspended in anhydrous dimethylformamide (3 mL), under inert atmosphere, and the resulting suspension is added with imidazole (0.980 g, 1.44 mmol). The mixture is stirred for 10' minutes, subsequently triethylsilyl chloride (TES-Cl) (0.193 mL, 1.15 mmol) is dropped therein, followed by addition of 4-dimethylamino pyridine (DMAP) (0.040 g 0.287 mmol). After 46 h, the reaction mixture is evaporated under vacuum, (TLC control of the complete disappearance of the reagent, eluent $CH_2Cl_2/MeOH=30/1$). The solid is subsequently redissolved in $CH_2Cl_2$ and washed with 1120 and saturated $NH_4Cl$. The aqueous phase is extracted with $CH_2Cl_2$ (2×10 mL). The organic phases are combined and dried over $Na_2SO_4$, filtered and concentrated under vacuum, thereby obtaining the desired product (0.133 g, 0.287 mmol) as a pale yellow solid.

$^1$H NMR ($CDCl_3$, 400 MHz) δ 8.37 (s, 1H, Ar, 8.25 (d, 1H, J=8.4 Hz, Ar), 7.92 (d, 1H, J=8.0 Hz, Ar), 7.82 (t, 1H, J=8.0 Hz, Ar), 7.65 (t, 1H, J=8.4 Hz, Ar), 7.57 (s, 1H, H-14), 5.67 (d, 1H, J=16.4 Hz, H-17), 5.29 (s, 2H, H-5), 5.25 (d, 1H, J=16.4 Hz, H-17), 2.00-1.84 (m, 2H, H-19), 1.03-0.93 (m, 12H), 0.80-0.71 (m, 6H). $^{13}$C NMR ($CDCl_3$, 100 MHz) δ 171.7, 157.6, 152.5, 151.5, 149.0, 145.9, 130.9, 130.4, 130.0, 128.4, 128.1, 128.0, 127.9, 118.9, 94.4, 75.3, 66.0, 50.0, 33.2, 7.9, 7.2, 6.4.

Example II

Preparation of 5-di-t-butoxycarbonylhydrazino-20-OTES-camptothecin

Camptothecin 20-OTES (0.100 g, 0.216 mmol) is dissolved in anhydrous THF (6 mL) with stirring under inert atmosphere, then cooled to a temperature of −78° C. and a 1.0 M LiHMDS solution in THF (0.281 mL, 0.281 mmol) is dropped therein. After 20', di-tert-butylazo dicarboxylate (DTBAC) (0.075 g, 0.324 mmol) in anhydrous THF (2 mL) is added. After 4 h at −78° C., the disappearance of the reagent is monitored by TLC (Hexane/AcOEt=3/1). Formation of the two diastereomers is observed. The reaction is quenched by addition of saturated $NH_4Cl$. The aqueous phase is extracted with $CH_2Cl_2$ (3×15 mL) and the organic phases are combined, dried over $Na_2SO_4$, filtered and concentrated under vacuum. The residue is purified by flash chromatography ($SiO_2$, Hexane/AcOEt=3/1), thereby obtaining a mixture of the two isomers (0.145 g, 0.210 mmol, 97%). The two isomers are separated by further chromatography. In order of elution:

1$^{st}$ diastereomer: $^1$H NMR ($CDCl_3$, 400 MHz) δ 8.80 (br s, 1H, Ar), 8.23 (d, 1H, J=8.4 Hz, Ar), 8.01 (br d, 1H, Ar), 7.90-7.71 (m, 2H, Ar), 7.70-7.45 (m, 2H, Ar+H-14), 6.52 (br s, 1H, H-5), 5.61 (d, 1H, J=16.8 Hz, H-17), 5.23 (d, 1H, J=16.8 Hz, H-17), 2.03-1.81 (m, 2H, H-19), 1.79-1.08 (br s, 18H), 1.06-0.92 (m, 12H), 0.80-0.70 (m, 6H). $^{13}$C NMR ($CDCl_3$, 100 MHz) δ 171.7, 157.8, 155.5, 155.5, 152.0, 152.0, 151.2, 149.4, 145.0, 132.1, 130.6, 130.0, 128.7, 128.4, 127.9, 119.9, 98.2, 82.7, 81.5, 79.7, 75.2, 65.7, 33.2, 28.3, 27.6, 7.7, 7.2, 6.4.

2$^{nd}$ diastereomer: $^1$H NMR ($CDCl_3$, 400 MHz) δ 8.79 (br s, 1H, Ar), 8.23 (d, 1H, J=8.4 Hz, Ar), 8.01 (br d, 1H, Ar), 7.85-7.76 (m, 2H, Ar), 7.65 (br t, 1H, J=8.4 Hz, Ar), 7.52 (s, 1H, H-14), 6.54 (br s, 1H, H-5), 5.61 (d, 1H, J=16.8 Hz, H-17), 5.22 (d, 1H, J=16.8 Hz, H-17), 2.03-1.82 (m, 2H, H-19), 1.76-1.08 (br s, 18H), 1.04-0.92 (m, 12H), 0.80-0.70 (m, 6H). $^{13}$C NMR ($CDCl_3$, 100 MHz) δ 171.5, 157.9, 155.5, 155.5, 152.3, 152.0, 151.2, 149.4, 145.1, 132.1, 130.6, 130.0, 128.7, 128.4, 127.9, 119.9, 98.2, 82.9, 81.5, 79.6, 75.2, 65.8, 33.3, 28.3, 27.4, 7.8, 7.2, 6.4.

Example III

Preparation of 5-di-t-butoxycarbonylhydrazino-20-OH-camptothecin 1$^{st}$ Diastereomer 5-di-t-Butoxycarbonylhydrazino-20-OTES-camptothecin (0.050 g, 0.072 mmol) first diastereomer is dissolved in anhydrous THF (4 mL) with stirring under inert atmosphere, subsequently $Et_3N.3HF$ (0.088 mL, 0.542 mmol) is dropped therein. The reaction mixture is reacted for 35 h at room temperature, monitoring by TLC the disappearance of the reagent (Hexane/AcOEt=3/2). The solvent is evaporated off under vacuum and the residue is purified by flash chromatography ($SiO_2$, Hexane/AcOEt=3/2), thereby obtaining the desired compound (0.041 g, 0.071 mmol, 98%) as a pale yellow solid.

The product is further purified by crystallization from $CH_2Cl_2$/Pentane=1/50.

$^1$H NMR ($CDCl_3$, 400 MHz) δ 8.77 (br s, 1H, Ar), 8.16 (br d, 1H, J=8.0 Hz, Ar), 7.97 (br s, 1H, Ar), 7.86-7.50 (m, 4H, Ar), 6.51 (br s, 1H, H-5), 5.66 (d, 1H, J=16.4 Hz, H-17), 5.24 (d, 1H, J=16.4 Hz, H-17), 3.86 (br s, 1H, OH), 2.00-1.80 (m, 2H, H-19), 1.79-1.13 (br s, 18H), 1.03 (t, 3H, J=7.6 Hz, Me). $^{13}$C NMR ($CDCl_3$, 100 MHz) δ 173.7, 157.9, 155.5, 155.5, 152.1, 151.3, 150.7, 149.6, 145.7, 132.3, 130.7, 129.9, 128.7, 127.9, 127.6, 120.0, 97.9, 82.8, 81.6, 79.7, 72.7, 66.1, 31.8, 28.3, 27.7, 7.7.

Example IV

Preparation of 5-di-t-butoxycarbonylhydrazino-20-OH-camptothecin 2$^{nd}$ Diastereomer 5-di-t-Butoxycarbonylhydrazino-20-OTES-camptothecin (0.050 g, 0.072 mmol) 2$^{nd}$ diastereomer is dissolved in anhydrous THF (4.5 mL) with stirring under inert atmosphere, subsequently $Et_3N.3HF$ (0.088 mL, 0.542 mmol) is dropped therein. The reaction mixture is reacted for 35 h at room temperature, monitoring by TLC the disappearance of the reagent (Hexane/AcOEt=3/2). The solvent is evaporated off under vacuum and the residue is purified by flash chromatography ($SiO_2$, Hexane/AcOEt=3/2), thereby obtaining the desired compound (0.040 g, 0.069 mmol, 96%) as a pale yellow solid.

The product is further purified by crystallization from $CH_2Cl_2$/Pentane=1/50.

$^1$H NMR ($CDCl_3$, 400 MHz) δ 8.79 (br s, 1H, Ar), 8.22 (br d, 1H, J=8.4 Hz, Ar), 7.99 (br s, 1H, Ar), 7.88-7.50 (m, 4H, Ar), 6.53 (br s, 1H, 1'-5), 5.65 (d, 1H, J=16.4 Hz, H-17), 5.26 (d, 1H, J=16.4 Hz, H-17), 3.80 (br s, 1H, OH), 2.00-1.80 (m, 2H, H-19), 1.79-1.13 (br s, 18H), 1.03 (t, 3H, J=7.2 Hz, Me).

$^{13}$C NMR (CDCl$_3$, 100 MHz) δ 173.6, 157.9, 155.4, 155.4, 152.1, 151.3, 150.8, 149.5, 145.6, 132.3, 130.8, 129.8, 128.7, 127.9, 127.8, 119.8, 98.0, 83.0, 81.5, 79.7, 72.7, 66.3, 31.8, 28.3, 27.7, 7.8.

Example V

Preparation of 5-dibenzyloxycarbonylhydrazino-20-OTES-camptothecin

Camptothecin 20-OTES (0.100 g, 0.216 mmol) is dissolved in anhydrous THF (6 mL) with stirring under inert atmosphere, then cooled to a temperature of −78° C. and a 1.0 M LiHMDS solution in THF (0.281 mL, 0.281 mmol) is dropped therein. After 20', dibenzyl azodicarboxylate (0.097 g, 0.324 mmol) in anhydrous THF (2 mL) is added. After 3 h at −78° C., temperature is left to raise to 25° C. and the disappearance of the reagent is monitored by TLC (Hexane/AcOEt=3/1). Formation of the two diastereomers is observed. After 90 min at room temperature, the reaction is quenched by addition of saturated NH$_4$Cl. The aqueous phase is extracted with CH$_2$Cl$_2$ (3×15 mL) and the organic phases are combined, dried over Na$_2$SO$_4$, filtered and concentrated under vacuum. The residue is purified by flash chromatography (SiO$_2$, Hexane/AcOEt=4/1 then 7/2), thereby obtaining a pale yellow solid (0.161 g, 0.212 mmol, 98%). The two isomers are separated by further chromatography. In order of elution:

1$^{st}$ diastereomer: $^1$H NMR (CDCl$_3$, 400 MHz) δ 8.70 (br s, 1H, Ar), 8.39 (br s 1H, Ar), 8.22 (br d, 1H, J=7.6 Hz, Ar), 7.95 (br d, 1H, J=7.6 Hz, Ar), 7.83 (br t, 1H, J=7.6 Hz, Ar), 7.65 (br t, 1H, J=7.6 Hz, Ar), 7.64-7.00 (m, 11H, Ar+H-14), 6.49 (br s, 1H, H-5), 5.57 (d, 1H, J=16.4 Hz, H-17), 5.47-4.44 (m, 5H), 1.98-1.82 (m, 2H, H-19), 1.02-0.89 (m, 12H), 0.80-0.70 (m, 6H). $^{13}$C NMR (CDCl$_3$, 100 MHz) δ 171.6, 158.0, 156.3, 156.3, 153.0, 152.2, 151.0, 149.6, 144.8, 135.3, 132.1, 130.6, 130.0, 128.6-127.8 (11C), 119.9, 98.4, 79.5, 75.2, 68.4, 67.9, 65.6, 33.0, 7.9, 7.2, 6.4.

2$^{nd}$ diastereomer: $^1$H NMR (CDCl$_3$, 400 MHz) δ 8.85 (br s, 1H, Ar), 8.58 (br s 1H, Ar), 8.20 (br s, 1H, Ar), 7.93 (br s, Ar), 7.81 (br t, 1H, J=7.6 Hz, Ar), 7.63 (br t, 1H, J=7.6 Hz, Ar), 7.56-6.90 (m, 11H, Ar+H-14), 6.52 (br s, 1H, H-5), 5.55 (d, 1H, J=16.8 Hz, H-17), 5.44-4.71 (m, 5H), 1.98-1.80 (m, 2H, H-19), 1.05-0.90 (m, 12H), 0.81-0.70 (m, 6H). $^{13}$C NMR (CDCl$_3$, 100 MHz) δ 171.5, 157.9, 156.4, 156.4, 152.9, 152.4, 150.9, 149.4, 144.8, 135.3, 132.1, 130.6, 129.9, 128.6-127.8 (11C), 119.9, 98.5, 79.3, 75.2, 68.4, 67.8, 65.6, 32.9, 7.8, 7.2, 6.4.

Example VI

Preparation of 5-dibenzyloxycarbonylhydrazino-20-OH-camptothecin 1$^{st}$ Diastereomer 5-Dibenzyloxycarbonylhydrazino-20-OTES-camptothecin 1$^{st}$ diastereomer (0.140 g, 0.184 mmol) is dissolved in anhydrous THF (6 mL) with stirring under inert atmosphere, subsequently Et$_3$N.3HF (0.225 mL, 1.380 mmol) is dropped therein. The reaction mixture is reacted for 52 h at room temperature, monitoring by TLC the disappearance of the reagent (Hexane/AcOEt=1/3). The solvent is evaporated off under vacuum and the residue is purified by flash chromatography (SiO$_2$, Hexane/AcOEt=1/1 then 2/3), thereby obtaining (0.113 g, 0.175 mmol, 95%) of the desired compound as a pale yellow solid. The product is further purified by crystallization from CH$_2$Cl$_2$/Pentane=1/50.

$^1$H NMR (CDCl$_3$, 400 MHz) δ 8.67 (br s, 1H, Ar), 8.39 (br s 1H, Ar), 8.12 (br d, 1H, J=7.6 Hz, Ar), 7.95 (br s, 1H, Ar), 7.74 (br t, 1H, J=7.6 Hz, Ar), 7.65-6.66 (m, 12H, Ar+H-14), 6.48 (br s, 1H, H-5), 5.55 (d, 1H, J=16.0 Hz, H-17), 5.42-4.44 (m, 5H), 3.86 (br s, 1H, OH), 1.92-1.72 (m, 2H, H-19), 0.95 (t, 3H, J=7.6 Hz, Me). $^{13}$C NMR (CDCl$_3$, 100 MHz) δ 173.5, 158.0, 156.2, 156.0, 153.0, 150.9, 150.9, 149.5, 145.3, 135.4, 132.2, 130.7, 129.8, 128.7-127.8 (11C), 119.9, 98.2, 79.6, 72.7, 68.5, 68.0, 65.9, 31.6, 7.8.

Example VII

Preparation of 5-dibenzyloxycarbonylhydrazino-20-OH-camptothecin 2$^{nd}$ Diastereomer 5-Dibenzyloxycarbonylhydrazino-20-OTES-camptothecin 2$^{nd}$ diastereomer (0.140 g, 0.184 mmol) is dissolved in anhydrous THF (6 mL) with stirring under inert atmosphere, subsequently Et$_3$N.3HF (0.150 mL, 0.921 mmol) is dropped therein. The reaction mixture is reacted for 55 h at room temperature, monitoring by TLC the disappearance of the reagent (Hexane/AcOEt=3/2). The solvent is evaporated off under vacuum and the residue is purified by flash chromatography (SiO$_2$, Hexane/AcOEt=1/1), thereby obtaining the desired compound (0.113 g, 0.175 mmol, 95%) as a pale yellow solid. The product is further purified by crystallization from CH$_2$Cl$_2$/Pentane=1/50.

$^1$H NMR (CDCl$_3$, 400 MHz) δ 8.71 (br s, 1H, Ar), 8.34 (br s 1H, Ar), 8.18 (br s, 1H, Ar), 7.94 (br s, 1H, Ar), 7.79 (br t, 1H, J=7.6 Hz, Ar), 7.70-6.70 (m, 12H, Ar+H-14), 6.52 (br s, 1H, H-5), 5.53 (d, 1H, J=16.4 Hz, H-17), 5.44-4.48 (m, 5H), 3.87 (br s, 1H, OH), 1.90-1.70 (m, 2H, H-19), 0.99 (t, 3H, J=7.6 Hz, Me). $^{13}$C NMR (CDCl$_3$, 100 MHz) δ 173.4, 158.0, 156.3, 156.1, 153.0, 151.0, 150.9, 149.6, 145.3, 135.5, 132.3, 130.8, 129.8, 128.7-127.8 (11C), 119.8, 98.4, 79.5, 72.7, 68.5, 67.8, 66.0, 31.6, 7.7.

Example VIII

Preparation of 4,5-dihydro-triazole[5,4-c]16a-deoxocamptothecin TFA Salt 5-di-t-Butoxycarbonylhydrazino-20-OTES-camptothecin (0.225 g, 0.324 mmol, 1:1 diastereomeric mixture) is dissolved in anhydrous 1,2-dichloroethane (DCE) (8 mL) with stirring under inert atmosphere, subsequently trifluoroacetic acid (TFA) (0.895 mL, 11.67 mmol) is dropped therein. The reaction mixture is reacted for 20 h at room temperature, monitoring by TLC the disappearance of the reagent (Hexane/AcOEt=1/3), then refluxed for 4 h. The solvent is evaporated off under vacuum and the residue is purified by flash chromatography (SiO$_2$, CH$_2$Cl$_2$/MeOH=30/1), thereby obtaining the desired compound (0.084 g, 0.178 mmol, 55%) as the trifluoroacetate salt. The 1:1 mixture of the two diastereomers is further purified by flash chromatography (SiO$_2$, Toluene/AcOEt=1/1).

$^1$H NMR (CDCl$_3$, 400 MHz) δ 10.61 (br s, 0.5H, N5–NH=C16a), 10.39 (br s, 0.5H, N5–NH=C16a), 8.67 (s, 1H, Ar, H-7), 8.22-8.15 (m, 1H, Ar), 7.96-7.92 (m, 1H, Ar), 7.88-7.78 (m, 1H, Ar), 7.69-7.60 (m, 2H, Ar), 6.38-6.36 (m, 1H, Ar, H-5), 5.72-5.62 (m, 1H, Ar, H-17), 5.32-5.20 (m, 2H, Ar, H-17+N5H), 4.08-3.86 (br s, 1H, OH), 1.96-1.74 (m, 2H, H-19), 1.05-0.98 (t, 3H, J=7.6 Hz, Me). $^{13}$C NMR (CDCl$_3$, 100 MHz) δ 173.8 (0.5C), 173.4 (0.5C), 159.1, 159.0, 156.7 (q CF$_3$COOH), 156.5 (q CF$_3$COOH) 151.5, 151.3, 150.7, 150.5, 150.1, 149.9, 144.8, 144.7, 134.0, 133.8, 131.6, 131.5, 129.9, 129.8, 128.7, 128.7, 128.4, 128.4, 128.2, 128.2, 127.1, 126.9, 120.5, 120.3, 99.1 (2C), 78.9, 78.6, 72.7, 72.7, 66.0 (2C), 31.7 (2C), 7.7, 7.7.

Example IX

Preparation of triazole[5,4-c]16a-deoxocamptothecin

The 4,5-dihydro-triazole[5,4-c]16a-deoxocamptothecin TFA salt (0.020 g, 0.042 mmol) is dissolved in anhydrous $CH_2Cl_2$ (4 mL) with stirring under inert atmosphere, subsequently 2,3-dichloro-5,6-diciano-p-benzoquinone (DDQ) (0.025 mg, 0.110 mmol) is added thereto. The reaction mixture is reacted for 31 h at room temperature, monitoring by TLC the disappearance of the reagent ($CH_2Cl_2$/MeOH=30/1). The reaction is quenched by addition of $H_2O$. The aqueous phase is extracted with $CH_2Cl_2$ (3×15 mL) and the organic phases are combined, dried over $Na_2SO_4$, filtered and concentrated under vacuum. The residue is purified by flash chromatography ($SiO_2$, $CH_2Cl_2$/MeOH=45/1), thereby obtaining a yellow solid (0.014 g, 0.039 mmol, 94%).

$^1$H NMR ($CDCl_3$, 400 MHz) δ 8.89 (s, 1H, Ar, H-7), 8.20 (d, 1H, J=8.4 Hz, Ar), 8.00 (d, 1H, J=8.4 Hz, Ar), 7.88 (t, 1H, J=8.4 Hz, Ar), 7.79 (s, 1H, Ar H-14), 7.69 (t, 1H, J=8.4 Hz, Ar), 5.70 (d, 1H, J=17.2 Hz, H-17), 5.28 (d, 1H, J=17.2 Hz, H-17), 3.83 (br s, 1H, OH), 2.00-1.74 (m, 2H, H-19), 1.08 (t, 3H, J=7.6 Hz, Me). $^{13}$C NMR ($CDCl_3$, 100 MHz) δ 172.6, 157.4, 152.5, 150.8, 148.9, 143.7, 134.9, 132.5, 132.4, 130.0, 129.5, 128.7, 127.5, 122.6, 121.4, 101.2, 72.4, 66.0, 31.6, 7.7.

Example X

Cell Growth Inhibition Assay

H460 Cells from human large cell lung tumor were cultured in RPMI-1640 medium containing 10% foetal calf serum. Cell sensitivity was determined by cell growth inhibition assay after 1 or 72 hr drug exposure. The cells in logarithmic growth were collected and seeded in duplicate in 6-wells plates. Twenty-four hours after seeding, cells were exposed to the drugs and counted with a Coulter conter 72 hours after exposure to the drugs for the determination of $IC_{50}$s. $IC_{50}$ is defined as the concentration inhibiting by 50% cell growth compared with untreated controls growth.

Example XI

Topoisomerase-I-Dependent DNA Rupture Assay

DNA ruptures were determined using a 751-bp BamHI-EcoRI DNA SV40 purified gel (Beretta G L, Binaschi M, Zagni A N D, Capuani L, Capranico G. Tethering a type IB topoisomerase to a DNA site by enzyme fusion to a heterologous site-selective DNA-binding protein domain. Cancer Res 1999; 59:3689-97). DNA fragments were only labeled at 3'. The DNA rupture reaction (20,000 cpm/sample) was carried out in 20 ml of 10 mM Tris-HCL (pH 7.6), 150 mM KCl, 5 mM $MgCl_2$, 15 μg/mL BSA, 0.1 mM thiothreitol, and the human recombinant enzyme (full length top1) for 30 min at 37° C. The reactions were blocked using 0.5% SDS and 0.3 mg/mL K proteinase for 45 min. at 42° C. DNA damage persistence was tested at different times adding 0.6M NaCl after 30 min. incubation with 10 μM of the drug. After precipitation, DNA was resuspended in denaturation buffer (80% formamide, 10 mM NaOH, 0.01 M EDTA and 1 mg/mL dye) before seeding in desaturating gel (7% polyacrylamide in TBE buffer). All of DNA rupture levels were measured by means of a PhosphoImager model 425 (Molecular Dynamics) (Dallavalle S, Ferrari A, Biasotti B, et al. Novel 7-oxyiminomethyl camptothecin derivatives with potent in vitro and in vivo antitumor activity. J Med Chem 2001; 44:3264-74).

| | Persistence of DNA damage (%) | | | |
|---|---|---|---|---|
| | | Time (min) | | |
| Compounds | 0 | 1 | 5 | 10 |
| Topotecan | 100 | 65 | 20 | 10 |
| Camptothecin | 100 | 58 | 23 | 20 |
| SN38 | 100 | 60 | 33 | 28 |
| IDN 6132 | 100 | 45 | 32 | 20 |

The invention claimed is:

1. Compounds of general formula (I):

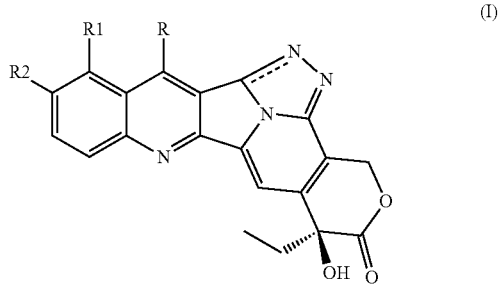

(I)

wherein:
  R is alkyl, aminoalkyl, hydroxyalkyl, nitrile, alkoxymino, aryloxymino, silylalkyl;
  R1 is hydrogen, hydroxy, alkoxy, aminoalkyl;
  R2 is hydrogen, hydroxy, alkoxy, aminoalkyl, optionally protected hydroxyl;
  wherein the alkyl, alkoxy, aminoalkyl or alkoxymino groups can contain 1 to 8 carbon atoms, in a straight or branched chain, whereas the aryloxymino group can contain 5 to 10 carbon atoms;
  the pharmaceutically acceptable salts, isomers, enantiomers, diastereomers thereof and corresponding mixtures.

2. Compounds of general formula (I):

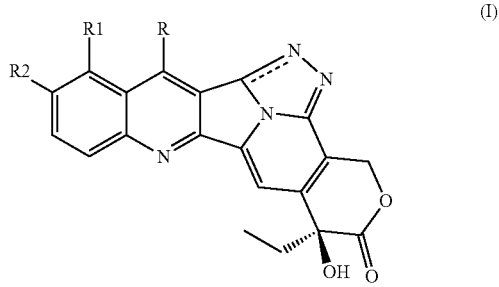

(I)

wherein:
  R is alkyl, aminoalkyl, hydroxyalkyl, nitrile, alkoxymino, aryloxymino, silylalkyl;
  R1 is hydrogen, hydroxy, alkoxy, aminoalkyl;
  R2 is hydrogen, hydroxy, alkoxy, aminoalkyl, optionally protected hydroxyl;
  wherein the alkyl, alkoxy, aminoalkyl or alkoxymino groups can contain 1 to 8 carbon atoms, in a straight or branched chain, whereas the aryloxymino group can contain 5 to 10 carbon atoms;

the pharmaceutically acceptable salts, isomers, enantiomers, diastereomers thereof and corresponding mixtures, which is selected from the group consisting of:
a) 4,5-dihydro-triazole[5,4-c]16a-deoxocamptothecin, and
b) triazole[5,4-c]16a-deoxocamptothecin.

3. A process for the preparation of the compounds of formula (I), which process substantially comprises steps (a)-(e) shown in the following scheme:

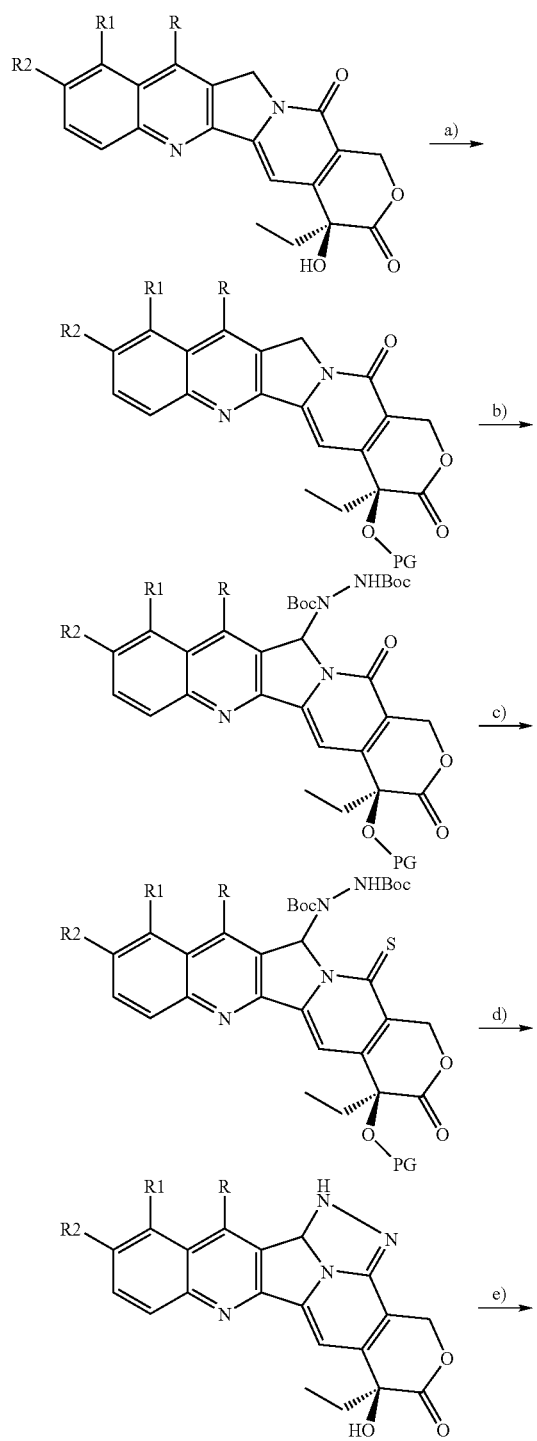

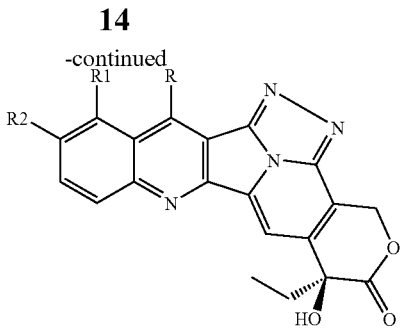

wherein:
a) protection of precursor hydroxy groups;
b) derivatization at 5- with N,N-diprotected hydrazine;
c) optional conversion of the pyridone ring to thiopyridone ring;
d) removal of the protective groups with concomitant cyclization;
e) optional aromatization of the pyrazole ring;
and wherein R is alkyl, aminoalkyl, hydroxyalkyl, nitrile, alkoxymino, aryloxymino, silylalkyl;
R1 is hydrogen, hydroxy, alkoxy, aminoalkyl;
R2 is hydrogen, hydroxy, alkoxy, aminoalkyl, optionally protected hydroxyl; while PG is a hydroxy-protective group.

4. The process for the preparation of compounds of formula (I) as claimed in claim 3, in which the order of the steps (b) and (c) is reversed.

5. A pharmaceutical composition containing a compound of formula (I) as claimed in claim 1 together with pharmaceutically acceptable carriers and excipients.

6. A pharmaceutical composition as claimed in claim 5, which is in a form suited to the oral or parenteral administration.

7. A method for the preparation of a drug for the treatment of tumors comprising preparing a compound of formula (I) as claimed in claim 1.

8. A method for the treatment of solid tumors comprising administering to a subject a compound of formula (I) as claimed in claim 1.

9. A method for treatment of solid tumors comprising mixing a compound of formula (I) as claimed in claim 1 together with pharmaceutically acceptable carriers and excipients to form a drug and administering the drug to a subject.

10. The compound of formula (I) as claimed in claim 1, wherein the alkyl, alkoxy, aminoalkyl or alkoxymino groups can contain 1 to 4 carbon atoms, in a straight or branched chain, whereas the aryloxymino group can contain 5 to 10 carbon atoms.

11. The method of claim 8 wherein the tumors are selected from the group consisting of tumors of the lung, ovary, breast, stomach, liver, prostate, soft tissues sarcomas, esophagus, pancreas, head and neck, glioblastoma, chronic and acute myelocytic leukemias.

12. The method of claim 9 wherein the tumors are selected from the group consisting of tumors of the lung, ovary, breast, stomach, liver, prostate, soft tissues sarcomas, esophagus, pancreas, head and neck, glioblastoma, chronic and acute myelocytic leukemias.

* * * * *